United States Patent [19]

Tu et al.

[11] Patent Number: 4,816,339
[45] Date of Patent: Mar. 28, 1989

[54] MULTI-LAYERED POLY(TETRAFLUOROETHYLENE)/ELASTOMER MATERIALS USEFUL FOR IN VIVO IMPLANTATION

[75] Inventors: Roger H. Tu, Lake Forest; Edwin Wang, Irvine, both of Calif.

[73] Assignee: Baxter International Inc., Deerfield, Ill.

[21] Appl. No.: 43,326

[22] Filed: Apr. 28, 1987

[51] Int. Cl.$^4$ ................................................ A61F 1/24
[52] U.S. Cl. .................................... 428/421; 428/422; 623/1; 623/11; 623/66; 427/2
[58] Field of Search ............... 428/422, 421; 427/2; 623/1, 11, 66; 128/334 R

[56] References Cited

U.S. PATENT DOCUMENTS

| | | |
|---|---|---|
| 3,527,650 | 9/1970 | Block .................................. 427/2 X |
| 4,193,138 | 3/1980 | Okita .................................. 427/2 X |
| 4,229,838 | 10/1980 | Mano .................................. 427/2 X |
| 4,286,341 | 9/1981 | Greer et al. ......................... 427/2 X |
| 4,718,907 | 1/1988 | Karwoski et al. .................... 427/2 X |

Primary Examiner—Nancy A. B. Swisher
Attorney, Agent, or Firm—Michael C. Schiffer; Richard L. Myers; W. Dennis Drehkoff

[57] ABSTRACT

Biologically compatible materials capable of being formed into implants, comprising layers of poly(tetrafluoroethylene) and mixtures of poly(tetrafluoroethylene) and elastomer, having excellent compliance, strength, elasticity and suturability are disclosed. The materials are preferably prepared as implants or vascular grafts by co-extruding a relatively thin luminal layer of poly(tetrafluoroethylene) having a distinct fibral nodal microstructure within a layer of a mixture of poly(tetrafluoroethylene) and elastomer to impart elasticity to the implant. A preferred embodiment comprises a radially asymmetric composite vascular graft having a luminal layer of poly(tetrafluoroethylene), a second layer of poly(tetrafluoroethylene)/elastomer mixture, a third layer of elastomer, and a fourth layer of a monomer fibrous elastomer matrix with each layer having a distinctive pore size, pore shape and porosity to promote tissue ingrowth and periprosthetic tissue anchoring.

42 Claims, 6 Drawing Sheets

MULTI-LAYERED POLY(TETRAFLUOROETHYLENE)/ELASTOMER MATERIALS USEFUL FOR IN VIVO IMPLANTATION

BACKGROUND OF THE INVENTION

Co-pending application Ser. No. 892,271 entitled "POROUS HIGHLY EXPANDED FLUOROPOLYMERS AND PROCESS THEREFOR", incorporated herein by reference, discloses the use of elastomers which strengthen expanded poly(tetrafluoroethylene) fibrils by forming a continuous matrix interpenetrating the microstructure of the fibrils. In so doing, it renders the poly(tetrafluoroethylene) structure porous but yet durable with excellent pliability for use as a vascular graft. More importantly, however, addition of an elastomer to the poly(tetrafluoroethylene) allows an implant or preferably, a vascular graft made from the material to be biologically compatible with surrounding tissue.

This invention relates to a multi-layered polytetrafluoroethylene/elastomer material that can be formed into an implant where there is an improvement in the luminal hydrophobicity, suturability, compliance, strength and elasticity due to the novel arrangement of respective layers of poly(tetrafluoroethylene), polytetrafluoroethylene/elastomer and elastomer. This invention relates to materials utilized in the production of devices for in vivo implantation, such as heart valve leaflets, sutures, vascular access devices or any related products, but more particularly relates to vascular grafts.

Conventional vascular grafts manufactured from porous poly(tetrafluoroethylene) have limitations in their strength and compliance. The porous grafts do not hold or resist dilation unless wrapped with a reinforcing film for support. This reinforcement slows down the tissue ingrowth preventing rapid healing. This is because of the relatively low radial tensile strength of poly(tetrafluoroethylene). In addition, the grafts are stiff and non-compliant to the natural artery.

Prior art patents disclose vascular grafts with laminated materials which are bonded in a manner to place porous, compacted poly(tetrafluoroethylene) in a position to be in contact with the blood surrounded by a layer of a suitable biocompatible material so that the implant allegedly may be accepted by the surrounding tissue. U.S. Pat. No. 4,576,608 describes a vascular graft having two layers, an inner layer comprising a blend of poly(tetrafluoroethylene) fibers and resin having a specific porosity wherein the outer layer comprises a fused blend of poly(tetrafluoroethylene) fibers and carbon fibers or silicone rubber. Other suitable biocompatible materials used in the lamination may be Teflon FEP, manufactured by DuPont Company or other biocompatible fabrics such as polyamide, polyaramid, polyimide or polyester fabric. U.S. Pat. No. 4,321,711 discloses a vascular prosthesis comprising porous tubing of poly(tetrafluoroethylene) containing an anti-coagulant substance and bonded to its outside surface, a porous elastomer coating containing a substance which counteracts the anti-coagulant. Typically, the anti-coagulant substance is heparin. Any heparin antagonist such as protamine may be used in the elastomer coating to counteract the heparin. The elastomer is typically fluorine rubber, silicone rubber, etc. While prior art implants may be porous and flexible, they do not provide the strength, elasticity or biological compatibility of the natural artery. There is a need for an in vivo implantable material that can be formed into a vascular graft which mimics the natural artery composition of collagen and elastin and is acceptable to the surrounding tissue.

SUMMARY OF THE INVENTION

It is an object of this invention to provide a multilayered poly(tetrafluoroethylene)/elastomer material for use as an implant where there is improved luminal hydrophobicity, compliance, strength and elasticity.

Another object of this invention is to provide shaped products manufactured from poly(tetrafluoroethylene) and an elastomer that are biologically compatible with surrounding tissue.

And yet another object of the present invention is to provide an in vivo implantable material having two, three or four layers of material for improved compatibility.

Multi-layered shaped articles, including medical implants such as vascular grafts may be produced from poly(tetrafluoroethylene) and an elastomer selected from the group consisting of polyvinylidene fluoride co-hexafluoropropylene, poly(tetrafluoroethylene-co-perfluoro(methylvinylether)), poly(tetrafluoroethylene-co-propylene), poly(vinylidene-co-chlorotrifluoroethylene), silicones, fluorosilicones, fluoroalkoxy phosphazenes, segmented copolyester ether, styrene butadiene block copolymers, polyethers, acrylonitrile butadienes, isoprenes, polyurethanes, and mixtures thereof.

The biologically compatible material of the present invention has excellent compliance, strength and elasticity because of the arrangement of layers of poly(tetrafluoroethylene), poly(tetrafluoroethylene)/elastomer, elastomer and fibrous elastomers.

The products comprising the instant invention have a very broad application in biomedical devices, such as artificial skin, vascular grafts, vascular acess devices, transcutaneous access devices, synthetic heart valve leaflets, and ligament/tendon implants, etc. In a preferred embodiment, each layer of the implant can be distinguished from other layers by having different pore size, pore shape and porosity. Indeed, the fibral-nodal microstructure throughout the matrix may have the internodal distance, i.e. pore size, in one section at least twice that for its adjacent sections. An in vivo material having four layers, for example, the internodal distance of the pores of luminal layer of poly(tetrafluoroethylene) is about 20 to about 30 microns. The internodal distance of the pores of second layer comprising a mixture of poly(tetrafluoroethylene) and elastomer may range from about 30 to about 500 microns, preferably about 50 to about 100 microns. The pore size is excellent for fibroblast tissue ingrowth, instead of undesired encapsulation, as the healing process progresses. The optional third layer of the graft comprises elastomer applied by spraying or dipping. The internodal distance of this layer approximates that of the second layer. Preferably, the outer or fourth layer comprises a polymer fibrous elastomer matrix with a pore size of about 100 to about 2000 microns, preferably about 200 to about 500 microns. The large pore size and high porosity provide an excellent site for periprosthetic tissue anchoring.

The less hydrophobic second layer provides excellent adhesive sites for bonding a hydrophilic outer layer to make a final composite with asymmetric hydrophobicity.

As described above, one embodiment of the present invention includes in vivo implantable material comprising the luminal and second layer previously described. Another embodiment of the present invention includes the luminal, second and fourth layer of material previously described. Another embodiment of the present invention includes all four layers previously described. Another embodiment comprises a luminal layer of poly(tetrafluoroethylene)/elastomer mixture and a second layer of poly(tetrafluoroethylene).

Devices used for in vivo implantation are defined as any device which may be used in chronic care situations wherein the device may be implanted into the body for long periods of time, i.e. months or longer. Further, the devices may be used for critical care situations for short periods of time, hours, days or weeks. The devices do not have to be totally implanted within the body to be considered within the scope of the present invention, for example, with no intention to be limiting catheters, any transcutaneous tubing or artifical skin may be included in the scope of the present invention.

DETAILED DESCRIPTION OF THE INVENTION

Figure 1:
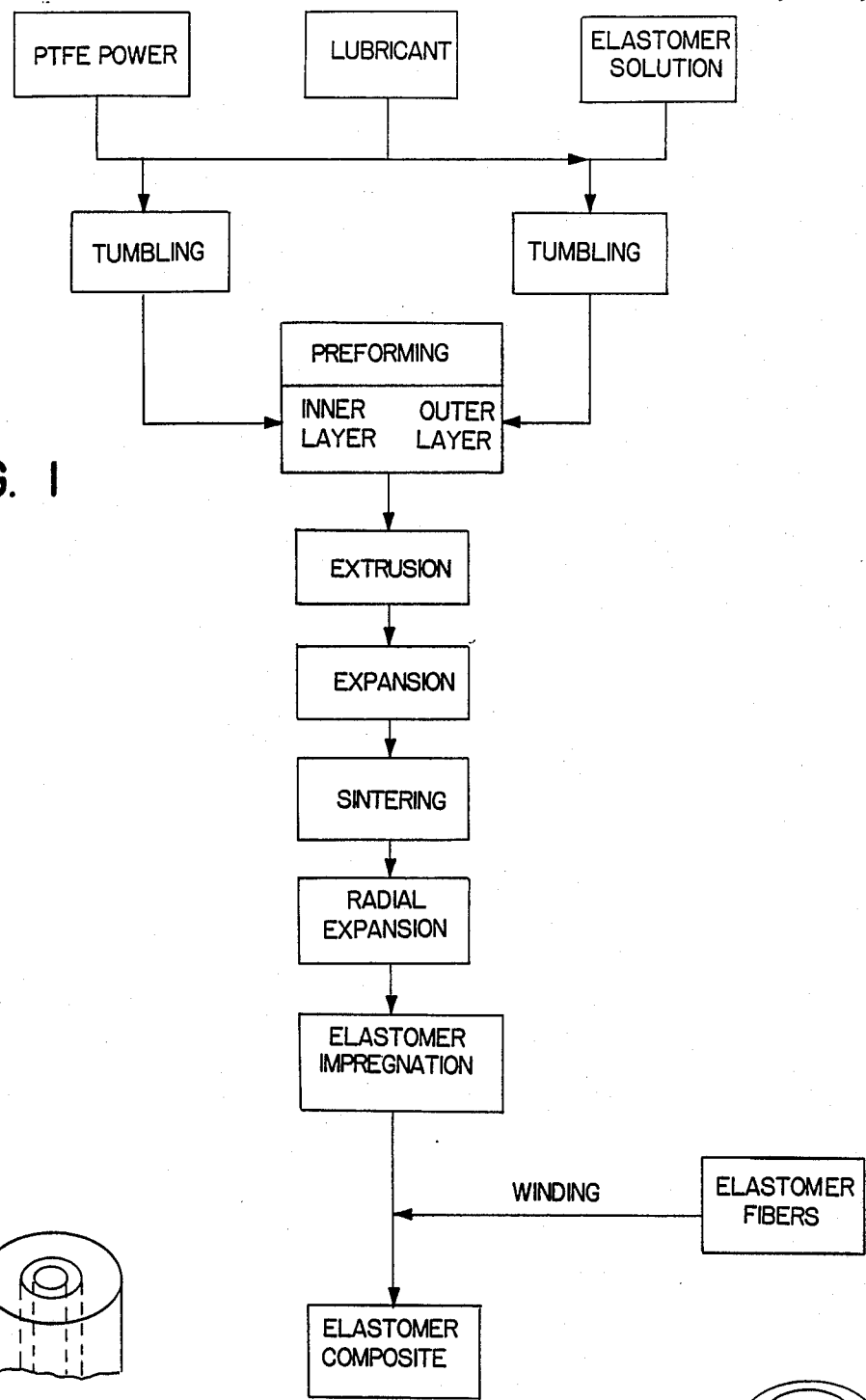
FIG. 1 is a schematic representation of the process of making the implants of the present invention.

The multi-layered poly(tetrafluoroethylene)/elastomer material produced in accordance with the present invention provides an improvement in luminal hydrophobicity, suturability, compliance, strength and elasticity. The luminal layer of poly(tetrafluoroethylene) provides the basic hydrophobic, blood compatible fibril-nodal microstructure.

The second layer, a mixture of poly(tetrafluoroethylene) and elastomer, provides a porous composite matrix as a transitional phase between the inner poly(tetrafluoroethylene) layer and outer elastomer layer. The addition of the elastomer to the poly(tetrafluoroethylene) renders the poly(tetrafluoroethylene) less hydrophobic in the second layer which provides a better opportunity for the material to be compatible with its in vivo environment. The less hydrophobic surface of the second layer is essential for the bonding of another material onto a pure poly(tetrafluoroethylene) substrate, the luminal layer.

The optional third layer of elastomer provides a hydrophilic tissue-compatible porous layer which promotes the elasticity, strength and suturability for the whole composite. The elastomer is admixed with a conventional solvent such as 1,1,1 trichloroethane, tetrahydrofuran or Freon, depending on the specific elastomer. The solvent penetrates the pores of the second layer and evaporates to allow the pore shape and size to remain relatively intact.

A preferred embodiment comprises a fourth layer of polymer elastomer fibers wraped onto the next adjacent layer. The outer elastomer layer of spirally bound fibers forms a non-woven matrix with large pore sizes which provides an excellent site for periprosthetic tissue anchoring. This is in contrast to the outer surface of the luminal layer of poly(tetrafluoroethylene) which does not promote tissue ingrowth and has little bonding strength.

In the multi-layered arrangement, when the material is shaped into a vascular graft, the graft mimics the natural artery composition of collagen, which is needed for strength, and elastin, which is needed for elasticity. Implants made from the asymmetric composite material of this invention undergo endotheliazation rapidly as a result of enhanced tissue ingrowth.

In accordance with the present invention, it has been found that composite materials can be paste formed, preformed, extruded as layers, dried, and expanded by stretching under certain conditions to produce medical devices for in vivo implantation. The process includes the formation of a poly(tetrafluoroethylene) layer, a second layer of poly(tetraflurorethylene) and elastomer mixture, and optionally third layer of an elastomer, which may impregnate the second layer and may be applied by spraying or dipping. The elastomer is preferably selected from the group consisting of polyvinylidene fluoride co-hexafluoropropylene, poly(tetrafluoroethylene-co-perfluoro(methylvinylether)), poly(-tetrafluoroethylene-co-propylene), poly(vinylidene-co-chlorotrifluoroethylene), silicones, fluorosilicones, fluoroalkoxy phosphazenes, segmented copolyester ether, styrene butadiene block copolymers, polyethers acrylonitrile butadienes, isoprenes, polyurethanes, and mixtures thereof. The elastomer may be added to the poly(-tetrafluoroethylene) in amounts effective to produce the desired results in a medical implant. Preferably, these amounts range from about 5% by weight to about 120% by weight of the poly(tetrafluoroethylene). Preferably, the amount of elastomer that can be added to the poly(-tetrafluoroethylene) to produce the desired result of this invention is about 50% by weight of the poly(tetrafluoroethylene) for the second layer of the medical implant and about 25% by weight of the poly(tetrafluoroethylene) for the impregnation of the elastomer or the spraying of the elastomer to form a third and optional layer. A preferred outer layer comprises elastomer fibers wound onto the next adjacent layer which could be the optional third layer of elastomer or second layer of poly(tetrafluoroethylene)-elastomer mixture. Compliance is increased by elastoer present in the second, third and fourth layers. This provides for excellent hydrophilicity for improved tissue compatibility in the outer layers while the luminal layer has the required hydrophobicity to be compatible with blood.

While any of the aforementioned elastomers function in this invention, a co-polymer of propylene and tetrafluoroethylene, poly(tetrafluoroethylene-co-propylene), sold under the trade name Aflas manufactured by Asahi Glass Company is preferred. The structure in which the tetrafluoroethylene and propylene arrange alternately in an orderly manner is shown:

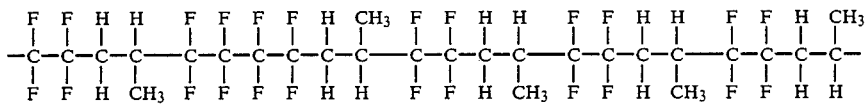

Another preferred elastomer is silicone.

The porous structure of the second layer of the material of this invention is composed of fine fibers of poly(tetrafluoroethylene) coated with the elastomer. The elastomer encapsulates and reinforces the poly(tetrafluoroethylene) fibrils. The elastomer is a continuous matrix interpenetrating the microstructure of the fibrils. It modifies the sharp edges of the fibrils and nodes to render the edges smooth. The smooth edges of the fibrils and nodes create a poly(tetrafluoroethylene) elastomer product resistant to suture tearing with high intrinsic elasticity. The pores are not individual, discrete openings. The are interconnected within the fibrils to provide for high porosity and relatively large pore size.

The asymmetric pore size differs with the individual layers. For example, the internodal distance of the pores of the luminal layer of poly(tetrafluoroethylene) is about 20 to about 30 microns. The internodal distance of the pores of the second layer may range from about 30 to about 500 microns, preferably about 50 to 100 microns. The pore size is ideal for fibroblast tissue ingrowth. The optional third layer, comprising poly(tetrafluoroethylene) generally retains the pore size and porosity of the second layer. The pores of optional fourth layer comprising a monomer fibrous elastomer have an internodal distance of about 100 to about 2000 microns, preferably about 200 to about 500 microns. The porosity of the entire material ranges from about 30% to 90%, preferably about 50% to about 90%. The large pore size of the fourth layer and high porosity provide an excellent side for periprosthetic tissue anchoring. The pore sizes of the various layers of the implantable material occur when the material is expanded at a ratio of about 50 to about 500%, preferably 250% during preparation.

Accordingly, the multi-layered matrix of the present invention may be obtained by producing a luminal layer of poly(tetrafluoroethylene) from poly(tetrafluoroethylene) powder and a second layer comprising lubricated poly(tetrafluoroethylene) powder admixed with an elastomer solution. Both the poly(tetrafluoroethylene) powder for the luminal layer and poly(tetrafluoroethylene)/elastomer mixtures are preformed. The elastomer dispersion should contain about 2 to about 10% by weight of the elastomer when mixing with the lubricated poly(tetrafluoroethylene) powder. Preferably, about 5% by weight of the elastomer dispersion is utilized to provide a mixture with poly(tetrafluoroethylene) and lubricant so that the elastomer is present in an amount equal to about 10% by weight of the poly(tetrafluoroethylene) in the blended powder. The amounts of each of the poly(tetrafluoroethylene) and elastomer needed to form the blended powder may be varied so that the elastomer may be present in the preliminary matrix in amounts ranging from about 5% to about 60% by weight of the finished product. Both the poly(tetrafluoroethylene) powder and the poly(tetrafluoroethylene) wetted with the elastomer solution are preformed and extruded together respectively to form separate layers. Alternately, the powder may be molded or rolled. For the paste extrusion process, the powder is compressed to form a pre-form or billet which is extruded under conditions of elevated temperature and pressure. The cut extrudate is then heated to a temperature between 35° C. and its crystalline melting point, 327° C., and expanded. Typically, the temperature is below the melting point of about 300° C. Expansion of the extrudate is accomplished biaxially or uniaxially. With reference to uniaxial expansion, the nodes are elongated, the longer axis of a node being oriented perpendicular to the direction of expansion. The fibrils are oriented parallel to the direction of expansion. The rate of stretch may vary and is not intended to be limiting. Preferably, the rate of stretch is 10% per second, however, it may range from 5% per second to about 100% per second. The materials can be expanded up to about 150 to about 600%, preferably about 350% of the original size in order to retain the excellent pore size and porosity previously described. For both the poly(tetrafluoroethylene) and the poly(tetrafluoroethylene)/elastomer layer, both layers can be stretched and retain their desired functionality when heated to 35° C. to 327° C., preferably about 300° C.

After expansion, the matrix is sintered by insertion into an oven at temperatures ranging from 342° C. to 390° C. for a short period of time. The sintered product, if in the form of tubing as generally described with an inner layer and an outer layer, may be radially expanded by conventional means. The tubing may be radially expanded by the means shown in co-pending application Ser. No. 935,237, which is incorporated herein by reference. The radial expansion of the inside diameter of the tubing may increase from about 5% to about 50%, preferably about 10 to about 50%. For example, if the inside diameter of the inner layer is 4 mm, it may be increased to 6 mm.

The radially expanded tubing may be placed in a bath of an elastomer solution containing from about 2% to about 10% by weight elastomer to form a third layer. Alternatively, the elastomer may be sprayed on the radially expanded tubing. From about 2% to about 25% by weight elastomer is added to the tubing at this time. The elastomer solution contains a solvent such as 1,1,1-trichloroethane or tetrahydrofuran, in an amount effective to allow the elastomer coat the second layer and free the pores of the second layer from which the solvent evaporates.

The elastomer impregnated tubing is loaded on a mandril. Elastomer fibers are wound and bonded onto the outer layer of the porous tubing. The fibers may be hydrophobic or hydrophilic. Hydrophobicity is arbitrarily refined as the % water absorption in 24 hours according to Americal Standards Teting Method D-570. The % water absorption should be less than 0.01. Examples of hydrophobic fibers, include but should not be limited to the following: silicones, butyl rubber, fluorocarbon elastomer, polyether polyurethane, etc. Examples of hydrophilic fibers, include but should not be limited to the following: polyester polyurethane, polyester elastomer (Arnitel brand from Akgo Chemical), poly(styrene-co-butadiene) and poly(ethylene-propylene-diene). The increase in weight of the tubing by the added fibers may range from 10% to 80% by weight, depending upon the number of passes of the elastomer fibers. The tubing is then removed from the mandril and allowed to dry.

As illustrated in FIG. 1, a typical process or producing a multi-layer poly(tetrafluoroethylene)/elastomer implant is described as follows:

Step 1—Blending: A lubrioated poly(tetrafluoroethylene) powder and lubricated poly(tetrafluoroethylene)/elastomer powder mixture are prepared. From about 12 to about 25% mineral oil may be added to the poly(tetrafluoroethylene) powder to add lubricity. The elastomer may be selected from the group consisting of polyvinylidene fluoride co-hexafluoropropylene, poly(tetrafluoroethylene-co-perfluoro(methylvinylether)), poly(tetrafluoroethylene-co-propylene), poly(vinylidene-co-chlorotrifluoroethylene), silicones, fluorosilicones, fluoroalkoxy phosphazenes, segmented copolyester ether, styrene butadiene block copolymers, polyethers, acrylonitrile butadienes, isoprenes, polyurethanes and mixtures thereof. Preferred elastomers are silicones and poly(tetra-fluoroethylene-co-propylene) sold under the trade name Aflas, manufactured by the Asahi Glass Company. Both are high temperature resistant elastomers. The elastomer is mixed with Freon TF to form a solution. From about 2 to about 10% elastomer is added to the solution. Further, the mineral oil lubricant is added to the solution in amounts ranging from about 5 to about 20% by weight. Further, the elastomer solution is added or sprayed upon a second amount of poly(tetrafluoroethylene) powder. From about 5 to about 50% of the elastomer by weight of the poly(tetrafluoroethylene) is added in solution to the poly(tetrafluoroethylene) powder. Both the lubricated poly(tetrafluoroethylene) powder and the poly(tetrafluoroethylene) powder wetted with the elastomer are mixed by tumbling in separate steps. A catalyst such as benzoyl peroxide may be added to provide elasticity and durability to the final product via crosslinking the elastomer portion. The catalyst is added in amounts ranging from about 0.01 to about 0.5% by weight of the poly(tetrafluoroethylene).

Step 2—Preforming: To manufacture tubing, a preferred embodiment of the present invention, a concentric tube is inserted inside the pre-former to divide the pre-former into two concentric spaces. The lubricated poly(tetrafluoroethylene) powder is loaded into the inner space while the lubricated poly(tetrafluoroethylene) powder/elastomer mixture is loaded into the outer space of the pre-former as shown in FIG. 1. In this application, the extrudate would have a relatively thin luminal layer of poly(tetrafluoroethylene) alone, having distinct fibril nodal microstructure for excellent blood contact as well as having luminal hydrophobicity for desired water entry pressure. The outer layer of poly(tetrafluoroethylene)/elastomer provides elasticity to improve compliance and as a transitional matrix to provide desired bonding between the inner and very outer layers. The powders are compressed to 50 to about 100 psi to form a dual layer pre-form or billet.

Step 3—Extrusion: The asymmetric pre-form is placed in an extruder which under hydraulic pressure forces the material out of the die. The extrudate is thin walled and flexible and not too rigid.

Step 4—Curing: The elastomer portion of the extrudate may optionally then be cured at a temperature of about 150° F. to about 350° F. for about 2 hours.

Step 5—Expansion: The extrudate is dried to evaporate the lubricant. Generally, the tubing is heated within a temperature range of about 35° C. to about 327° C., preferably to about 300° C. which is below the crystalline melting point of poly(tetrafluoroethylene) and expanded at a rate of about 5% per second to about 100% per second so that the final length is about 150 to about 600, preferably about 350% of the original length. Further, the tubing is sintered by being placed in a preheated oven at a temperature ranging from 342° C. to 390° C. for a relatively short period of time.

Step 6—Radial Expansion: The expanded sintered tubing is radially expanded by placement of the tubing over a tip-tapered mandril, as described in co-pending application Ser. No. 935,237. The inside diameter of the tubing, which is normally about 4 mm to about 8 mm, is radially expanded to be about 6 mm to about 10 mm. In this step, the poly(tetrafluoroethylene) fibril-nodes are relaxed in the radial direction so that the elastomer solely can contribute to the radial compliance. This radial expansion step may take place before or after the sintering of the tubing and to some degree, effects the asymmetry of the pores in the layers. The process may end at this point wherein the product exhibits excellent porosity, compliance, strength, elasticity, luminal hydrophobicity and biocompatibility. It is suitable for in vivo implantation and provided for good tissue ingrowth. For an improvement in various properties, the process may be continued to produce additional multi-layered products.

Step 7—Elastomer Impregnation: (Formation of the optional third layer) The tubing is dipped into a solution of elastomer so that the outer surface develops a layer of the elastomer as the third layer or possibly outer layer. The elastomer layer is porous to promote periprosthetic tissue ingrowth. In an elastomer solution containing about 5% by weight elastomer, and a solvent such as 1,1,1-trichloroethane in amounts ranging from about 1 to about 10% by weight of the solution, the tubing should be immersed for about 1 to about 10 minutes. It is not desired to have the elastomer permeate the poly(tetrafluoroethylene)/elastomer layer and migrate into the lumen. Alternatively, the elastomer solution may be sprayed on the poly(tetrafluoroethylene)/elastomer layer. The elastomer solution may optionally contain therapeutic agents including but not limited to antibiotic and/or hemostatic substances.

Step 8—Winding: (Formation of the optional fourth layer) A catalyst may optionally be added to the elastomer solution to aid in the curing. An elastomer solution or melt is pushed under pressure through a fine orifice forming a fiber. The orifice moves with respect to a rotating mandril. The fiber is thus wrapped on the mandril. However, the winding may be accomplished with a conventional apparatus when the fiber is wound around the tubing which is placed on a mandril. The angle of winding should be about 10 to about 85 degrees. The elastomer fiber wound around the tubing should form a porous nonwoven network because it is usually heated or containing a conventional solvent to promote fiber-fiber bonding when the fibers reach the mandril. Preferably, an elastomer is sprayed onto the fibers being wound on the mandril to promote fiber bonding. Typically, the fiber diameter may be from about 10 to about 200 microns, preferably about 20 to about 50 microns. Preferably, the fibers are poly(tetrafluoroethylene-co-propylene) or silicone or polyurethane or segmented copolyester ether or mixtures thereof. The winding angle for applying the fibers to the mandril may vary from about 10 to about 85 degrees, preferably from about 30 to about 75 degrees. The fibers may contain catalyst to aid in curing as conventionally known in the art. The fibers are porous and may contain pore structures different from the fibrilnodal microstructure seen in the other layers. The compliance of the tubing can be maintained by determining the amount of the elastomer added to the final product in relation to the weight of the poly(tetrafluoroethylene). Preferred ratios are about 5 to about 120%.

Step 9—Curing: Curing occurs at a temperature of about 150° to about 350° F. The product is then ready for cutting.

In an alternate embodiment, silicone elastomer and silicone fluid may be premixed with the poly(tetrafluoroethylene) powder and subjected to the aforementioned process. The silicone elastomer and the silicone fluid affects the final poly(tetrafluoroethylene) fibrilnodal micropores. The silicone fluid is not generally a lubricating oil, and should not be treated as such. In the composition, mineral oil should still be used as lubricant. The silicone fluid is removed from the materials during the high temperature expansion or sintering step. To produce a silicone fluid-free poly(tetrafluoroethylene)/elastomer product, ultrasonic leaching in 1,1,1-trichloroethane or Freon may be incorporated into the process.

Expansion of about 250% as shown in the above-described process, will produce an internodal distance of the luminal poly(tetrafluoroethylene) layer of about 20 to about 30 microns. The second layer of the material, containing the mixture of poly(tetrafluoroethylene) powder and elastomer dispersion, for example, silicone, plus the addition of the silicone fluid, which when evaporated would generate an internodal distance within the poly(tetrafluoroethylene)/elastomer intermediate layer of from 30 to about 500 microns, preferably about 50 to about 100 microns. The internodal distance shown in the second layer is excellent for fibroblast tissue ingrowth, rather than undesired encapsulation, as healing progresses.

After elastomer dipping or spraying, the last layer of elastomer fibers are added. The bonding fibers are spirally wound on the tubing to form a non-woven fibrous matrix with the pore size of about 100 to about 2000 microns, preferably about 200 to about 500 microns. The large pore size and high porosity provides an excellent site for periprosthetic tissue anchoring. This is an improvement over an outer surface of poly(tetrafluoroethylene) which does not promote tissue ingrowth and has little bonding strength.

In this embodiment, each layer has a different pore size, pore shape and porosity, all of which promotes tissue growth and tissue anchoring.

An alternate embodiment comprises a luminal layer of poly(tetrafluoroethylene)/elastomer and a second layer of poly(tetrafluoroethylene). This combination of layers provides for better hydrophillicity due to the elastomer in the luminal layer. Subsequently, the previously described third and fourth layers may be optionally be added.

Figure 2:
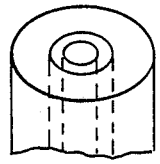
FIG. 2 is a perspective view of a schematic of one embodiment of an open end of an implantable vascular graft of the present invention.
Figure 6:
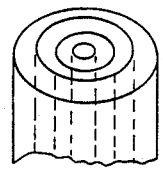
FIG. 6 is a perspective view of a schematic of one embodiment of an open end of an implantable vascular graft of the present invention.

FIGS. 2 and 6 show preferred embodiments of the present invention.

In all embodiments, the elastomer solution may contain therapeutically active substances, such as antibiotics or heparin that may be released into the surrounding environment.

FIG. 2 shows an embodiment of the present invention having a luminal poly(tetrafluoroethylene) layer and poly(tetrafluoroethylene)/elastomer outer layer.

FIG. 6 shows an embodiment of the present invention having the layers shown in FIG. 2 as well as an optional oute layer of elastomer fibers.

The following examples describe the processes and products within this invention as well as a further description of the properties of the porous tetrafluoroethylene polymers/elastomers. As indicated above, some of the properties of these porous mixtures are substantially different from the corresponding properties of conventionally extruded or molded tetrafluoroethylene polymers. As a result of these differences, the porous composite material is useful in many applications involving medical implants and vascular grafts.

EXAMPLE 1

This example describes the process of manufacturing a radially-asymmetric poly(tetrafluoroethylene)-elastomer composite vascular graft that consists of three concentric layers: poly(tetrafluoroethylene) luminal layer, poly(tetrafluoroethylene)-elastomer intermediate layer, and an elastomer fibrous outer layer. Elastomers such as Aflas elastomer, a copolymer of tetrafluoroethylene and propylene, manufactured by the Asahi Glass Company, can be used in the asymmetric composite material.

During the preforming stage, poly(tetrafluoroethylene) powder sold under the trade name Fluon CD123 and manufactured by ICI Americas, was lubricated with about 20% by weight on the final solid basis by mineral spirits. The poly(tetrafluoroethylene) powder was loaded into the inner concentric layer while a blend of lubricated 95% poly(tetrafluoroethylene)—5% Aflas elastomer mixture was loaded into the outer concentric layer. The divider in the preformer was thereafter removed without disturbing the layered powders. The asymmetric billet was extruded under conditions of temperature about 90° F. and pressure 500 psi to form extrudates having an internal diameter of 4 mm.

The extrudates were expanded 300% at an expansion rate of about 10% per second in an oven, at a temperature of 500° F. followed by flash sintering at a temperature of 700° F. for a time period of 5 minutes. The sintered asymmetric poly(tetrafluoroethylene)-Aflas extrudate or graft had a wall thickness of about 0.48 mm. and was coded 1A. The sintered graft was then radially enlarged from 4 mm. to 5 mm. inside diameter and impregnated with an Aflas elastomer solution in accordance with the procedures shown in co-pending patent application Ser. No. 935,237. The weight gain due to the addition of the elastomer during impregnation was 16% by weight. This graft was coded 1B.

Graft 1B was loaded on a mandril. Aflas elastomer fibers were then wound and bonded onto the poly(tetrafluoro-ethylene)-Aflas porous graft. The winding angle ranged from 10° to 80° with respect to the axial direction. The weight gain as a result of the Aflas elastomer fibers winding range from 30% to 80% depending upon the number of passes of Aflas fibers. The finished poly(tetrafluoroethylene)-elastomer composite graft was coded 1C. This manufacturing procedure follows the process shown in FIG. 1.

Both grafts 1A and commercially available Gore-Tex vascular graft, which served as a control, showed a compliance of less than $1.0 \times 10^{-2}$%/mmHg. For reference, a human femoral artery generally has a compliance, based on outside diameer measurement, of 5.9×10-2%/mmHg. As a result of post-processing procedures, that is, radial enlargement and elastomer impregnation, graft 1B showed an improved compliance at 1.9×10-2%/mmHg. The radially asymmetric poly(-tetrafluoroethylene)elastomer composite graft 1C exhibited a compliance range from 2.5 to 5.2×10-2%/mmHg, depending on how many passes of elastic fibers had been wound at a particular winding angle. In general, the high-angle winding provided radial tensile strength, kink resistance, suture retention strength, and aneurysm protection, whereas the low-angle winding provided longitudinal tensile strength and radial compliance.

The suture retention strength was measured for grafts 1A and 1C. Graft 1A maintained a high suture retention strength of 416 grams while the suture retention strength of the poly-(tetrafluoroethylene)-elastomer composite graft 1C showed a strength of 535 grams.

EXAMPLE 2

This example describes a process of manufacturing a radially-asymmetric vascular graft without outside fiber winding. A billet was prepared by loading about ⅔ of a lubricated poly(tetrafluoroethylene) powder into the outer concentric layer and about ⅓ of the lubricated mixture of 80% poly(tetrafluoroethylene) and 20% silicone elastomer into the inner concentric layer. The silicone elastomer was produced by diluting the silicone dispersion Q7-2213 from Dow Corning in 1,1,1-trichloroethane solvent. The 6 mm. inside diameter extrudate was cured with respect to silicone at 50° C. overnight. The cured extradate was expanded and sintered. It was coded 2A.

Figure 3:
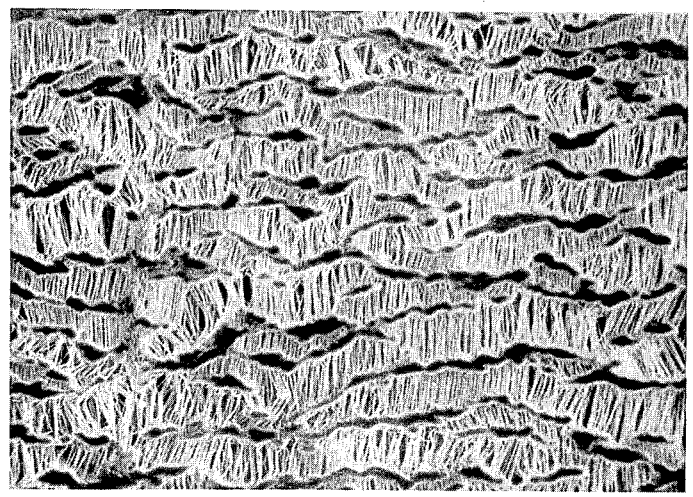
FIGS. 3 to 5 depict microphotographs of the implant of the present invention.

Sample 2A exhibits very typical fibril-nodal microstructure. The lumen surface was very smooth for the pre-cured graft. Another similar extrudate without curing was expanded and sintered. The lumen surface was very rough, probably due to the instability of uncured silicone when the extrudate was exposed to sudden high temperature. FIG. 3 shows the SEM lumen which consists of 80% poly(tetrafluoroethylene) and 20% silicone. Since silicone does not form the fibril-nodal structure as poly(tetrafluoroethylene) does, the silicone probably functions as a coating on the surface of the poly(tetrafluoroethylene) fibril-nodes.

A conventional water-entry pressure test was performed on Sample 2A. The water-entry pressure was 10.8 psi which is exceeedingly high. A comparable poly(tetrafluoroethylene) or homogeneous poly(tetrafluoroethylene)/elastomer graft with similar porosity would have a water-entry pressure of about 4–5 psi as a result of the poly(tetrafluoroethylene) hydrophobicity. This high-water entry pressure may conceivably be due to the self-sealing effect of silicone in a radially-asymmetric poly(tetrafluoroethylene) silicone composite graft. The self-sealing mechanism is desirable for a vascular access device such as an A-V fistula for hemodialysis purposes. It is speculated that silicone may seal the needle puncture of a poly(tetrafluoroethylene)-type device when silicone is sandwiched between layers of poly(tetrafluoroethylene). The porosity of Sample 2A was 66%.

EXAMPLE 3

A thin-wall 95% poly(tetrafluoroethylene)/5% Aflas elastomer tubing was prepared by following the manufacturing process of co-pending application Ser. No. 892,271 incorporated herein by reference. In this example, fibrous elastomer was wound onto the poly(tetrafluoroethylene)/elastomer to make an asymmetric poly(tetrafluoroethylene)/elastomer composite graft. During post-processing, the expanded/sintered poly(tetrafluoroethylene)/elastomer tubing was placed onto a mandril and secured in a winder. The spraying-and-winding technique consists of winding an elastomer fibers onto the tubing and spraying elastomer solution simultaneously to bond the fibers. This technique was utilized to firmly bond the outside fibers onto the poly(tetrafluoroethylene)/elastomer tubing. The composite graft consists of polyurethane fibers (300 passes at 65° winding angle with respect to the axial direction, the fibers diameter being about 50 microns) winding and Aflas elastomer solution spraying intermittently. The sample was coded 3A.

The 4 mm inside diameter graft of Sample 3A was very soft and flexible with good suture retention strength nd suturability. The graft was sterilized with ethylene oxide and used to replace a 4 cm portion of a canine femoral artery. The graft showed an in vivo compliance of about 5×10-2%/mmHg by using an electromagnetic rheoangiometry system. This measurement system is described in an article by S. Klein "Effect of Suture Technique on Arterial Anastomotic Compliance" Arch Surg. 117;45–47 (1982). The in vivo compliance of said compliant graft sample 3A compares favorably with that from the adjacent femoral artery of the same canine.

EXAMPLE 4

The process of Example 3 was followed except that during post-processing, the expanded/sintered poly(tetrafluoroethylene)/elastomer tubing was dip coated into the Aflas elastomer prior to fiber winding, rather than spraying the elastomer as in Example 3, and winding 375 passes of polyurethane fibers in comparison to 300 passes in Example 3. The 4 mm radially asymmetric poly(tetrafluoroethylene)/elastomer composite graft was coded 4A.

The graft was very soft and flexible with good suture retention strength of 248 grams. It had a burst strength of greater than 90 psi which is higher than a typical poly(tetrafluoroethylene) type vascular grafts. The outer elastomer fibers reinforce the graft. The longitudinal tensile strength for said graft was higher than 4000 psi whereas its radial tensile strength was more than 400 psi.

The graft exhibited an in vivo compliance of about 4×10-2%/mmHg by using the electromagnetic rheoangiometry system. The lower compliance as compared to Sample 3A in Example 3 was due probably to more fibers used in this graft 4A. In either case, the in vivo compliance was much higher than the control material, a Gore-Tex graft which is about 0.9×10-2%/mmHg.

EXAMPLE 5

The T-Peel Test

The objective of the T-peel test is to determine th relative peel resistance of an adhesive bond between two flexible adherents. The peel strength test involves a stripping of a flexible member of an assembly that has been bonded with an dhesive to another member that may be flexible or rigid. The T-peel test is described in ASTM Method D-1876. For present purposes the T-peel test was modified.

The specimens were Samples 4A taken from Example 4. The specimens were 0.5" wide and 1" long and bonded over ½" of their length. The test was performed on a standard tensile testing machine, manufactured by Precision Instrument, Inc., at a linear speed of 0.09" per second. The specimen showed a peeling strength of 296 grams. This bonding strength between the poly(tetrafluoroethylene) elastomer tubing and outer elastomer fibers was strong enough to hold the composite graft without delamination. Thus it appears, that the spraying-and-winding technique to bond the outer elastomer fibers onto the poly(tetrafluoroethylene)/elastomer tubing is adequate.

EXAMPLE 6

Dip-coating or spray-coating of elastomer onto the poly(tetrafluoroethylene) elastomer tubing was employed with the radially-asymmetric poly(tetrafluoroethylene)/elastomer composite graft and similar results were obtained. The poly(tetrafluoroethylene)/elastomer composite graft was dipped into Aflas elastomer, silicone elastomer, and Cardiothane 51, a copolymer of polyurethane and silicone manufactured by Kontron, Inc. The tubing was dip-coated into 3.5 weight % solutions of the elastomers. The compliance improvement of the thin-walled (0.2 mm) 95% poly(tetrafluoroethylene)/5% elastomer tubing is shown in the following table. The control sample was the same tubing without dip-coating.

| Elastomer Coating | Coating Thickness, mm | Compliance × 10-2%/mmHg |
| --- | --- | --- |
| Control | 0 | 1.3 |
| Aflas | 0.08 | 1.5 |
| Silicone | 0.13 | 1.7 |
| Cardiothane 51 | 0.05 | 1.8 |

In order to incrrese the distance between fibril micropores and therefore its pore size, silicone compatible fluid may be added and then removed from the poly(tetrafluoroethylene). This embodiment is shown in the following examples.

EXAMPLE 7

A mixture of 95% poly(tetrafluoroethylene), sold under the trade name Fluon CD-123 manufactured by ICI Americas and 5% by weight silicone sold under the trade name Q7-2213 manufactured by Dow Corning was prepared by adding 20% silicone fluid on a solid basis and tumbling for 1 hour. The silicone fluid is sold under the trade name 360 Medical Fluid manufactured by Dow Corning and has a 20 cs viscosity. The silicone fluid is a clear, colorless polydimethylsiloxane fluid. The mixture was loaded into the outer concentric layer of a pre-former. The inner concentric layer was loaded with poly(tetrafluoroethylene) powder lubricated with 20% by weight mineral spirit. The radially asymmetric powder was then compressed to 300 to 500 psi, and a solid billet was formed. The billet was placed in an extruder which, by hydraulic pressure, forces the mixture through an orifice. The extruded material was cut into sections having a length of approximately 5 in. and an inside diameter of 6 mm. The sections were loaded onto a rack in an expansion oven. They were cured for 2 hours at 150° F. and then overnight at 300° F. The sections were thereafter expanded to 20 inches at an expansion rate of about 10% per second while at an expansion temperature of about 500° F. The samples were sintered at 680° F. and coded 7-X. The last digit "X" indicates the sintering time in minutes.

EXAMPLE 8

Theoretically, the evaporation of a silicone fluid from a cured silicone elastomer matrix generates the unexpected large pores with long internodal distances in a poly(tetrafluoroethylene)/silicone composite. To determine the residual content of leachable silicone, which presumably includes the silicone fluid and/or silicone oligomers out of the silicone elastomer, the sintered poly(tetrafluoroethylene)/elastomer/silicone products were left in an ultrasonic cleaner, manufactured by Branson Instrument Co., filled with 1,1,1-trichloroethane. After 30 minutes leaching, the weight losses on sintered products with different sintering times are shown in the following table.

| Sample Code | Sintering Time | Weight Loss After Leaching |
| --- | --- | --- |
| 7-1 | 1 min. | 5.3% |
| 7-3 | 3 | 3.8 |
| 7-5 | 5 | 3.2 |
| 7-10 | 10 | 2.7 |
| 7-15 | 15 | 1.8 |
| 7-0 | 0 | 12.9 as control |

Apparently, most of the silicone fluid is removed during the high temperature expansion or sintering step.

EXAMPLE 9

Figure 4A:
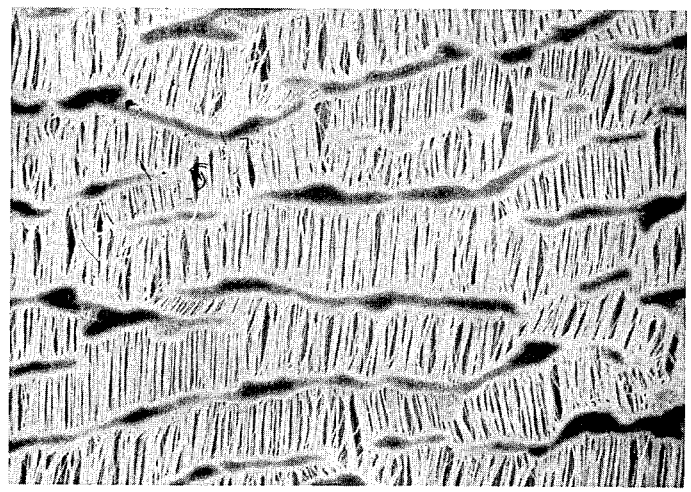
Figure 4B:
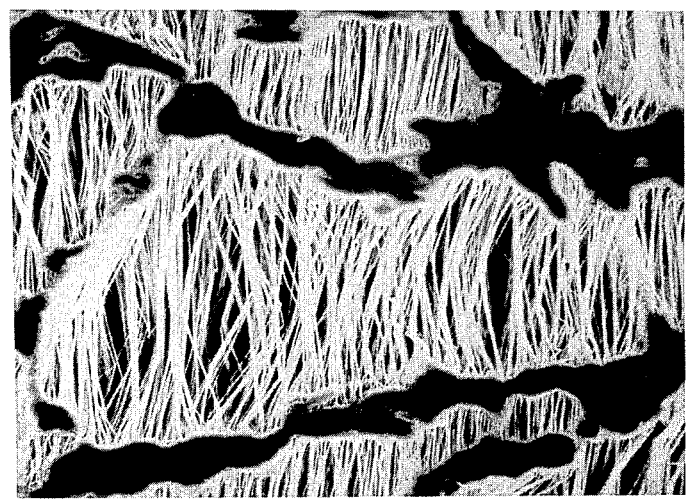
Figure 4C:
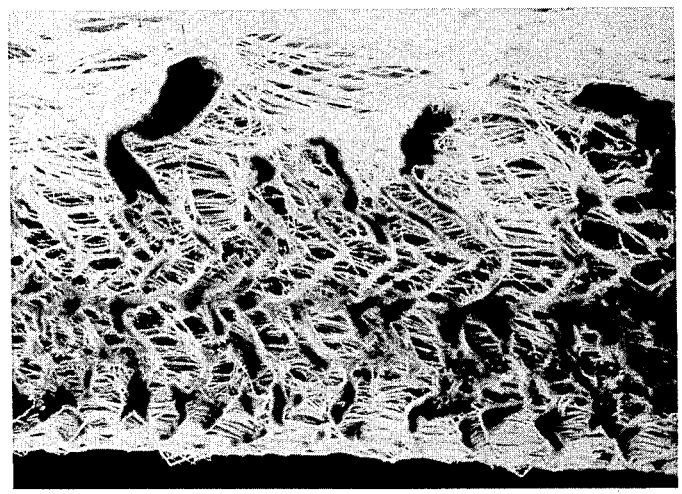

Samples 7-3 (3 min. sintering) and 7-15 (15 min. sintering) were examined with scanning electron microscopy. FIGS. 4A and 4B show the lumen surface and exterior surface of Sample 7-3. Both surfaces indicate typical poly(tetrafluoroethylene) fibril-nodal microstructure. The internodal distance of the lumen surface is measured at about 25 microns where the internodal distance of the exterior surface is about 60 microns. The cross-section scanning electron microscopy as shown in FIG. 4C clearly demonstrates that the outer layer has as much larger pores than the inner layer as a result of the instant innovative process.

Figure 4D:
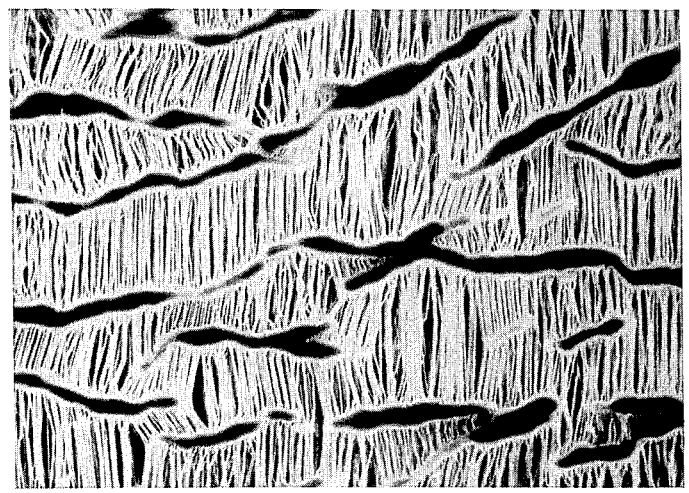
Figure 4E:
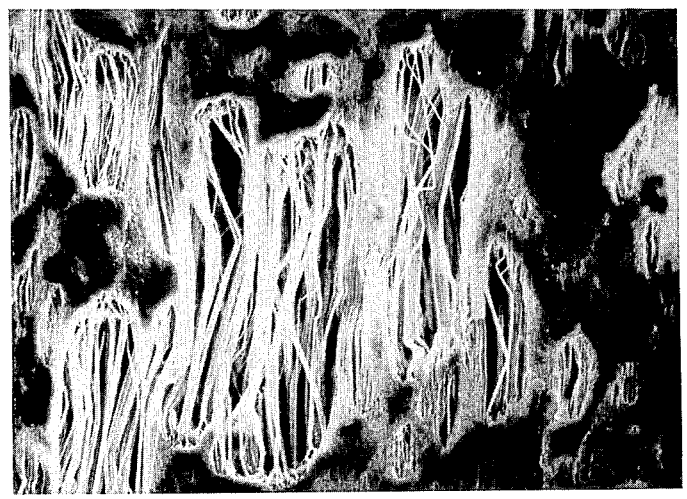
Figure 4F:

Similarly, a poly(tetrafluoroethylene)/elastomer/silicone sample which had been sintered at 680° F. for 15 minutes, Sample 7-15, showed asymmetric pore sizes. FIGS. 4D and 4E show the lumen surface and exterior surface for Sample 7-15. The internodal distance of said lumen surface is measured at about 25 microns where that of the exterior surfaces is about 90 microns. The cross-sectional scanning electron microscopy as shown in FIG. 4F confirms the distribution of the asymmetric pore sizes.

EXAMPLE 10

Figure 5A:
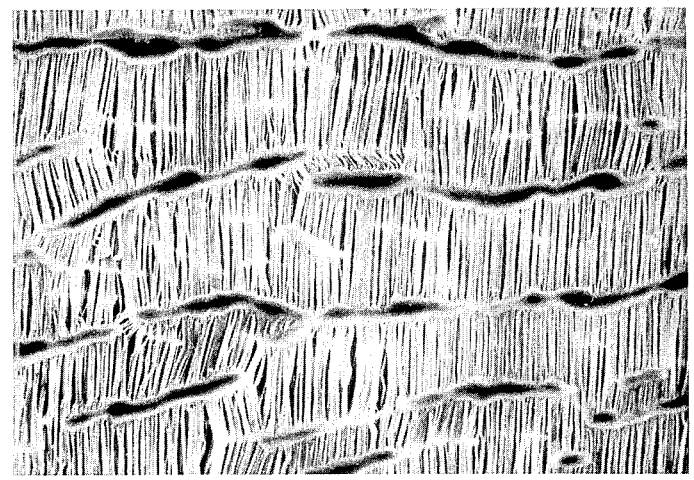
Figure 5B:
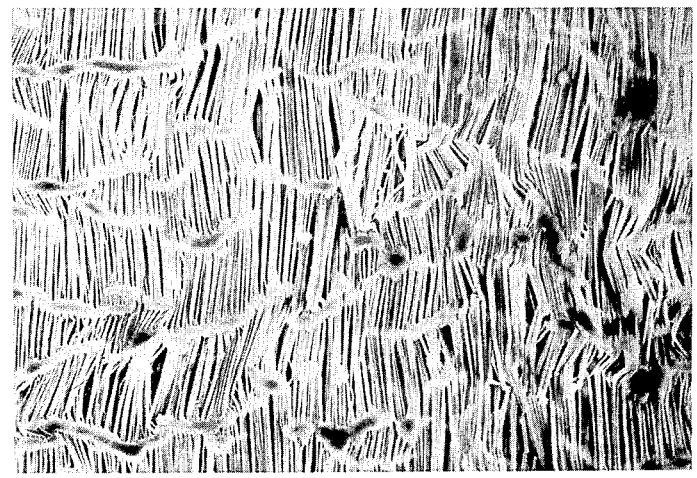
Figure 5C:
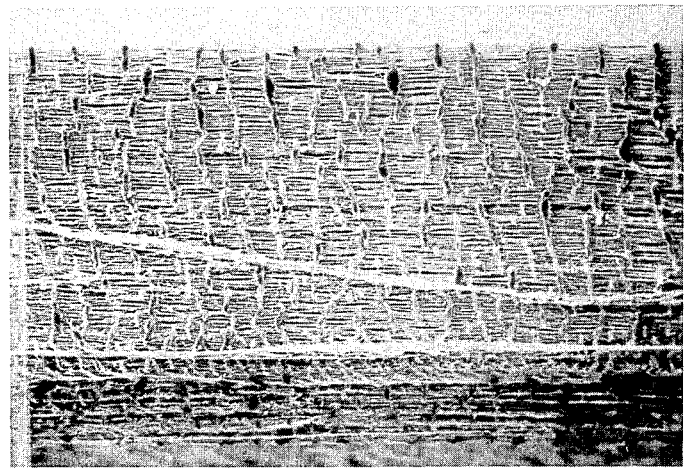

For our comparison purposes, an asymmetric poly(tetrafluoroethylene)/silicone product following the procedure of Example 6 was formulated, except that mineral oil, instead of silicone fluid, was used in both the poly(tetrafluoroethylene) and poly(tetrafluoroethylene)/silicone layers. The product was fabricated and coded as Sample 10. This sample, containing poly(tetrafluoroethylene) and 5% silicone was examined under scanning electron microscopy. FIGS. 5A and 5B show the lumen surface and exterior surface of Sample 10. Both indicate very typical poly(tetrafluoroethylene) fibral-nodal microstructures. The internodal distance is constant from the lumen side through to the exterior side as shown in a crosssectional scanning electron microscopy, FIG. 5C. The lumen is at the lower side of the figure. The internodal distance was measured at about 25 microns. No asymmetric pore sizes were observed.

EXAMPLE 11

A poly(tetrafluoroethylene)/elastomer product with asymmetric pore sizes in a sandwich type configuration was fabricated. The lubricated poly(tetrafluoroethylene)/silicone powder with silicone fluid is loaddd into the middle zone of a preformer. The adjacent zones are filled with a lubricated poly(tetrafluoroethylene) powder. The same process as described in Example 6 may be followed, preforming, extrusion, curing, expansion and sintering, to produce a poly(tetrafluoroethylene)/elastomer product with many large pores in the middle layer. The asymmetric large pores serve as a reservoir for elastomer deposition to produce an elastic poly(tetrafluoroethylene) product.

As described in detail herein above, the in vivo implantable material of this invention is an improvement over conventional implantable materials composed mainly of porous poly(tetrafluoroethylene) in that it provides compliance, suturability, elasticity and the required hydrophilicity to promote tissue ingrowth.

While the invention has been described in detail and with reference to specific embodiments thereof, it will be apparent to one skilled in the art that various changes and modifications can be made therein without departing from the spirit and scope thereof.

What is claimed is:

1. A biologically compatible multi-layered in vivo implantation material comprising
   a porous, luminal layer of poly(tetrafluoroethylene) and
   a second layer comprising a porous mixture of poly(tetrafluoroethylene) and elastomer.

2. The material in accordance with claim 1 in which the elastomer is selected from the group consisting of polyvinylidene fluoride co-hexafluoropropylene, poly(tetrafluoroethylene-co-perfluoro(methylvinylether)), poly(tetrafluoroethylene-copropylene), poly(vinylidene-co-chlorotrifluoroethylene), silicones, fluorosilicones, fluoroalkoxy phosphazenes, segmented copolyester ether, styrene butadiene block copolymers, polyethers acrylonitrile butadienes, isoprenes, polyurethanes and mixtures thereof.

3. The material in accordance with claim 1 in which has an elastomer content of from about 5% to about 120% by weight of the poly(tetrafluoroethylene).

4. The material in accordance with claim 1 in which the luminal layer has a porosity of about 30% to about 90% by volume.

5. The material in accordance with claim 1 wherein the internodal distance of the pores in the luminal layer ranges between about 20 to about 30 microns.

6. The material in accordance with claim 1 wherein the elastomer content of the second layer is about 5 to about 20% by weight of the second layer.

7. The material in accordance with claim 1 in which the second layer has a porosity of about 30% to about 90% by volume.

8. The material in accordance with claim 1 wherein the internodal distance of the pores in the second layer ranges between about 30 to about 500 microns.

9. The material in accordance with claim 7 in whioh the internodal distance of the pores in the second layer ranges between about 50 to about 100 microns.

10. The material in accordance with claim 1 wherein the internodal distance of the pores in the second layer is at least twice the internodal distance of pores in the luminal layer.

11. The material in accordance with claim 1 which is an asymmetric composite.

12. The material in accordance with claim 1 in which an elastomer is applied to the exterior surface of the second layer forming a third outer layer.

13. The material in accordance with claim 12 in which the elastomer is applied by immersing the material into an elastomer bath.

14. The material in accordance with claim 13 in which the bath comprises about 1 to about 10% by weight elastomer.

15. The material in accordance with claim 12 in which a solvent is admixed with the elastomer and applied to the exterior surface of the second layer to form a third layer.

16. The material in accordance with claim 12 in which an effective amount of solvent is admixed with said elastomer to provide for at least the same porosity and pore size as in the second layer.

17. The material of claim 12 in which the elastomer is selected from the group consisting of polyvinylidene fluoride co-hexafluoropropylene, poly(tetrafluoroethylene-co-perfluoro(methylvinylether)), poly(tetrafluoroethylene-copropylene), poly(vinylidene-co-chlorotrifluoroethylene), silicones, fluorosilicones, fluoroalkoxy phosphazenes, segmented copolyester ether, styrene butadiene block copolymers, polyethers acrylonitrile butadienes, isoprenes, polyurethanes and mixtures thereof.

18. The material in accordance with claim 13 in which the material is immersed in the bath for an effective amount of time to impregnate the second layer but not migrate with the luminal layer.

19. The material in accordance with claim 12 in which the third layer has the same porosity and internodal distance of the pores as the second layer.

20. The material in accordance with claim 12 in which the elastomer provides hydrophillicity to the material.

21. The material in accordance with claim 1 in which a therapeutically active substance is present in said elastomer.

22. The material in accordance with claim 12 in which a fibrous polymer elastomer matrix is applied to the exterior of the third layer forming a fourth layer.

23. The material in accordance with claim 22 in which the fibrous polymer elastomer matrix comprises hydrophilic or hydrophobic polymer.

24. The material in accordance with claim 23 in which the elastomer is selected from the group consisting of poly(tetrafluoroethylene-co-propylene), silicones, polyurethane, butyl rubber, fluorocarbon elastomer, polyether polyurethane, polyester polyurethane, polyester elastomer, poly(styrene-co-butadiene), and poly(ethylene-propylene-diene), and mixtures thereof.

25. The material in accordance with claim 24 in which the fibrous polymer elastomer matrix is applied to the outer layer by wrapping.

26. The material in accordance with claim 24 in which the fourth layer has a porosity of about 30% to about 90% by volume.

27. The material in accordance with claim 24 in which the internodal distance of the pores in the fourth layer ranges between about 100 to about 2000 microns.

28. The material in accordance with claim 1 in which the luminal layer comprises a porous mixture of poly(tetrafluoroethylene) and elastomer, and the second outer porous layer is poly(tetrafluoroethylene).

29. The material of claim 1 shaped as a medical device.

30. The material of claim 1 shaped as a medical device suitable for in vivo implantation.

31. The material of claim 1 shaped as a vascular graft.

32. The material of claim 12 shaped as a medical device.

33. The material of claim 12 shaped as a medical device suitable for in vivo implantation.

34. The material of claim 12 shaped as a vascular graft.

35. The material of claim 22 shaped as a medical device.

36. The material of claim 22 shaped as a medical device suitable for in vivo implantation.

37. The material of claim 22 shaped as a vascular graft.

38. A biologically compatible multi-layered in vivo implantation material comprising
a porous, luminal layer of poly(tetrafluoroethylene),
a second layer comprising a porous mixture of poly(tetrafluoroethylene and elastomer) and a third layer comprising an elastomer applied to the exterior surface of the second layer.

39. The material in accordance with claim 38 in which the elastomer is selected from the group consisting of polyvinylidene fluoride co-hexafluoropropylene, poly(tetrafluoroethyleneco-perfluoro(methylvinylether)), poly(tetrafluoroethylene-copropylene), poly(vinylidene-co-chlorotrifluoroethylene), silicones, fluorosilicones, fluoroalkoxy phosphazenes, segmented copolyester ether, styrene butadiene block copolymers, polyethers acrylonitrile butadienes, isoprenes, polyurethanes and mixtures thereof.

40. A biologically compatible multi-layered in vivo implantation material comprising a porous, luminal layer of poly(tetrafluoroethylene), a second layer comprising a porous mixture of poly(tetrafluoroethylene) and elastomer, a third layer comprising an elastomer applied to the exterior surface of the second layer and a fourth layer comprising a fibrous monomer matrix applied to the exterior of the third layer.

41. The material in accordance with claim 40 in which the fiberous polymer matrix is applied by wrapping.

42. The material in accordance with claim 40 in which the elastomer is selected from the group consisting of polyvinylidene fluoride co-hexafluoropropylene, poly(tetrafluoroethylene-co-perfluoro(methylvinylether)), poly(tetrafluoroethylene-co-propylene), poly(vinylidene-co-chlorotrifluoroethylene), silicones, fluorosilicones, fluoroalkoxy phosphazenes, segmented copolyester ether, styrene butadiene block copolymers, polyethers acrylonitrile butadienes, isoprenes, polyurethanes and mixtures thereof.

* * * * *